United States Patent [19]

Walker et al.

[11] Patent Number: 4,637,726
[45] Date of Patent: Jan. 20, 1987

[54] NONDESTRUCTIVE NONCONTACT DEVICE TO CHARACTERIZE SEMICONDUCTOR MATERIAL

[75] Inventors: Clifford G. Walker; George A. Tanton, both of Huntsville, Ala.

[73] Assignee: The United States of America as represented by the Secretary of the Army, Washington, D.C.

[21] Appl. No.: 699,282

[22] Filed: Feb. 7, 1985

[51] Int. Cl.$^4$ ........................................... G01N 21/21
[52] U.S. Cl. ................................... 356/367; 356/239
[58] Field of Search ................ 356/35, 364, 365, 366, 356/367, 368, 239

[56] References Cited

U.S. PATENT DOCUMENTS 4,498,780  2/1985  Banno et al. ..................... 356/440 X
4,559,451  12/1985  Curl .............................. 250/563 X

OTHER PUBLICATIONS

Smith, "Nonvisual Measurement of Collapse Field in Small-Bubble Garnets", *Rev. Sci. Instrum.*, vol. 52, No. 11, pp. 1737–1748, 11/81.

*Primary Examiner*—Davis L. Willis
*Assistant Examiner*—Matthew W. Koren
*Attorney, Agent, or Firm*—Freddie M. Bush; Robert C. Sims

[57] ABSTRACT

A wafer is positioned in a magnetic field. A computer initializes the light level and the electronic gain of each detector preamp associated with a fiber optic link from the analyzer. The magnetic field direction would then be reversed by computer command. This would cause a localized change in intensity of light passing through the wafer, due to Faraday Rotation (FR). The resulting change in detector output together with location and wavelength data could be used to compute a map of the wafer.

10 Claims, 1 Drawing Figure

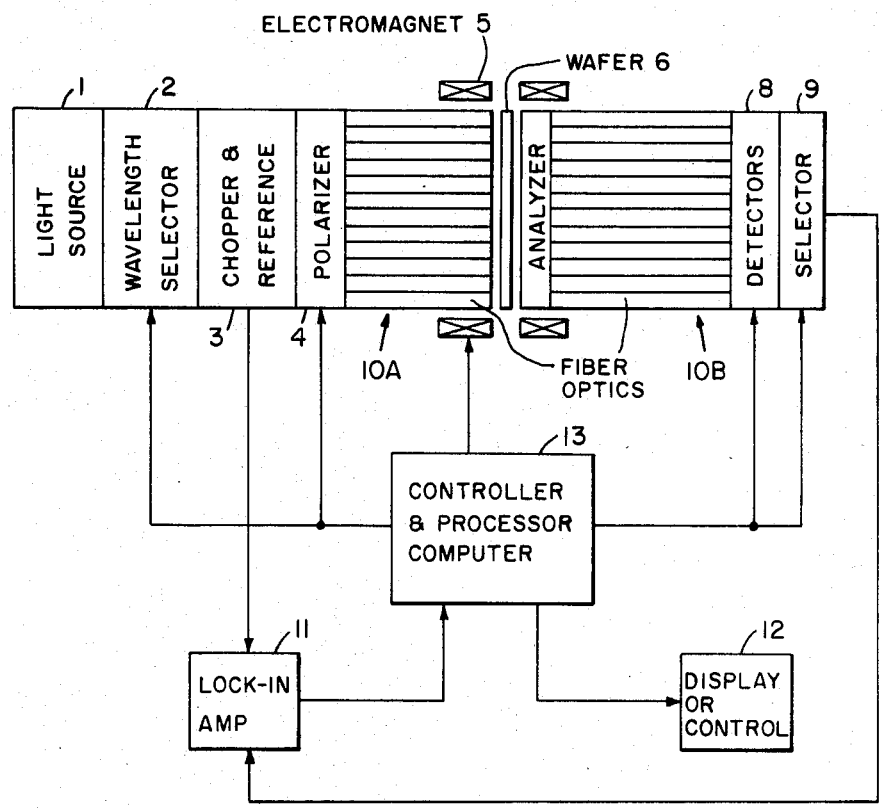

NONDESTRUCTIVE NONCONTACT DEVICE TO CHARACTERIZE SEMICONDUCTOR MATERIAL

DEDICATORY CLAUSE

The invention described herein may be manufactured, used, and licensed by or for the Government for governmental purposes without the payment to us of any royalties thereon.

BACKGROUND OF THE INVENTION

There is a need to screen semiconductor single crystal wafers (e.g., CdS, HgCdTe, GaAs) quickly and accurately in order to process them into detectors at the high rates required to meet projected production schedules at the lowest possible cost. For example, the present method of screening wafers requires making electrical contact to the wafer by physically bonding a dissimilar metal to the wafer surface. This technique is labor intensive and frequently causes mechanical and electrical problems that result in inaccurate and non-repeatable results. In contrast, the system described in this disclosure requires no physical contacts, is not labor intensive and can map the wafer with high spatial resolution thereby identifying small areas of nonuniformity that could not otherwise be found by conventional screening methods. Subject invention can characterize the wafer quickly with a much higher spatial resolution than conventional methods, thus greatly reducing time and cost now incurred from processing areas of a wafer unsuitable for detectors.

BRIEF DESCRIPTION OF THE DRAWING

The single FIGURE is a block diagram of the present invention.

DESCRIPTION OF THE BEST MODE AND PREFERRED EMBODIMENT

The device shown in the FIGURE consists of well regulated, collimated, light source 1, which directs light through a wavelength selector 2 and on through a chopper and reference device 3 which is used for synchronization and pulsing the light. The light from the source 1 now passes through a polarizer 4 and on to a plurality of optical fibers 10A which provides the input light sources to wafer 6. The corresponding number of fibers 10B is located on the other side of analyzer 7. These optical fibers are kept short in length so as not to substantially interfere with the polarization. A collimator may be used in place of fibers 10A.

The wafer 6 to be tested is located between the optical fibers 10A and the analyzer 7 and is subject to magnetic fields by electromagnet 5 which is broken up into two windings so as to allow room for the insertion of the wafer 6. When power is applied to the electromagnet 5 Faraday Rotation (FR) will occur in the wafer 6 and cause the polarization direction to rotate in accordance to characteristics of the wafer at its various points along the bundle of optical fibers 10A. An analyzer 7 will cause reduction in the light intensity in accordance to how much shift in polarization has been caused by the wafer 6. Also reduction due to the degree of transparency of the particular area of the wafer is realized. The analyzer is designed such that there will be little scattering of the light passing therethrough, so that the light passing through individual fibers of the bundle 10B will have an intensity change in light level only due to a small section of the wafer 6. Analyzer 7 is shifted at a polarization angle less than (or more than) 90° with respect to polarizer 4 by a value greater than the maximum amount of expected FR expected to be caused by wafer 6. In this way the variation in the output of detectors 8 when the magnetic field is reversed accumulates instead of canceling.

An array of detectors 8 equal in number to the number of fibers in fiber optical bundle 10B are provided. In effect the fiber optics 10B image the wafer onto detector 8. These detectors can also contain a plurality of preamplifiers for seletively ampilifying the electrical signal output. A selector circuit 9 is providing for sequentially selecting a particular output of a particular detector (which represents a particular area of wafer 6) and feeding it through lock-in amplifier 11 to the computer 13. Lock-in amplifier 11 cooperates with chopper 3 so as to synchronize the output of detector 8 with the pulsing provided by chopper 3, so that computer 13 receives the information at the maximum output time period. The controller and processor computer 13 is connected to control the wavelength of selector 2 the angle of the polarization of polarizer 4, the direction of the magnetic field from electromagnet 5 and the selection and amplification levels of the preamps output to be received from detector 8 and selector 9. A display and/or a control output 12 is provided.

OPERATION CYCLE

First the semiconductor wafer 6 to be tested is inserted between the split magnets 5. A holder can be provided for precise location of the wafer to be tested. The temperature of the wafer can be controlled by conventional means so as to lower the wafer's temperature to a predetermined value. The device is placed in the operational mode by applying power to light source 1 and computer 13. Initial direction and magnitude of the magnetic field H and light intensity $I_o$ passing from 1 through fiber optics bundle 10 to wafer 6, are selected respectively by the computer by controlled adjustments of the current through electromagnet 5 and angle between polarizer 4 and analyzer 7 which are rotated about a common axis. The computer is also programmed to initialize the sampling sequence by setting selector 9 to read the output from the first detector preamp 8 through lock-in amplifier 11, and to select the optimum chopping rate and probing wavelength by adjusting the wavelength selector 2 and chopper 3 respectively. After these initial conditions have been automatically established, the programmed testing of the wafer proceeds as follows:

The output level of the first detector is recorded. The direction of the magnetic field H is reversed on command from the computer 13. The computer records the level change of the first detector and also the location of the corresponding detector. Similarly, the location and change in output of each detector is sequentially recorded in the computer as the computer automatically changes the selector position of 9. Changes in the outputs of the detectors will be different if nonuniformities are present in the wafer. This is due to Farady rotation caused by free carriers in the crystal, and local defects in the lattice through which the light passes at any location. The intensity of light falling on a detector will be mathematically proportional to the Faraday rotation. At the conclusion of the sequencing operation, the computer will have acquired and stored the change in output of each of detectors 8 and the corresponding location of the parts of the wafer that caused the changes. From this information the computer will generate and display an intensity vs position map of the wafer that shows those parts of the wafer within predetermined specifications and automatically marks them using the peripheral 12. When desired, the entire process will be automatically repeated at several different wavelengths by programming the computer to adjust wavelength selector 2 before each sequencing operation. This will provide all necessary data for the computer to characterize the wafer and determine the free-carrier concentration.

In the case of a wafer which has nonuniform characterizes by design, a standard (reference) wafer will be analized and stored in the memory of computer 13 and the wafers to be tested can be compared with the reference wafer stored values. Any of the well known programmable computers of sufficient size can be programmed to perform the required functions.

We claim:

1. In a system for testing a device which will pass light therethrough, the improvement comprising a light source for producing light, a plurality of first fiber optics located between said light source and said device to be tested whereby light from said light source will be directed through said device to be tested in a plurality of different small areas of said device, a second plurality of second fiber optics positioned to individually receive light that passes through the different areas of said device to be tested, a plurality of detectors positioned to receive light form individual optical fibers of said second plurality of optical fibers so as to detect any change in the characteristics of the light cause by said device to be tested, a polarizer connected between said light source and said first plurality of optical fibers so as to polarize the light entering said second plurality of optical fibers and said device tested, magnetic means for providing a magnetic field across said device to be tested; and a polarizer analyzer positioned between said device to be detected and said second plurality of optical fibers whereby any Faraday rotation (FR) caused by said device to be tested will be detected by said detectors.

2. A system as set forth in claim 1 further comprising a selector means connected to said plurality of detectors so as to individually select and record the outputs of the detectors.

3. A system as set forth in claim 2 further comprising a controller and processor connected to said selector means for the determining which detector is to be selected and for storing the information detected, and said controller and processor connected to said magnetic means for reversing the magnetic field so as to provide a reverse FR reading of each area of said device to be detected.

4. A device as set forth in claim 3 further comprising a chopper positioned between said light source and said polarizers so as to pulse the output of said light source; and synchronizing means connected between said chopper, selector means and said controller and processor for synchronizing the selected outputs of the detectors.

5. A system as set forth in claim 4 further comprising a wavelength selector positioned between said light source and said chopper for determining the wavelength of the light to be passed through said device to be tested, and means connected to said wavelength selector and said controller and processor for controlling said wavelength selector.

6. A system as set forth in claim 5 whereby the controller processor in cooperation with the selector means provides a map of the device to be tested and an output display connected to the controller processor for displaying said map.

7. In a system for testing a device which will cause Faraday rotation (FR) of polarized light passing therethrough, the improvement comprising a light source for producing polarized light, a first means located between said light source and said device to be tested whereby light from said light source will be directed through said device to be tested, magnetic means positioned so as to produce a magnetic field through said device to be detected so as to cause FR of the polarized light passing through said device, and a plurality of detectors positioned to receive light from individual small areas of said device so as to detect any change in the characteristics of the polarized light cause by said device to be tested.

8. A system as set forth in claim 7 further comprising a controller means connected to said magnetic means so as to selectively reverse the direction of the magnetic field.

9. A system as set forth in claim 8 further comprising a polarizer analyzer positioned between said device to be detected and said detectors.

10. A system as set forth in claim 8 further comprising a conventional means for lowering the wafer temperature.

* * * * *